(12) United States Patent
Holgate et al.

(10) Patent No.: US 11,559,420 B2
(45) Date of Patent: Jan. 24, 2023

(54) PERSONAL AUGMENTATION SUIT AND METHOD FOR ASSISTED HUMAN MOTION WITH BACK DIFFERENTIAL ASSEMBLY

(71) Applicant: SpringActive, Inc., Tempe, AZ (US)

(72) Inventors: Matthew A. Holgate, Mesa, AZ (US); Jeffrey A. Ward, Phoenix, AZ (US); Chase Wheeler, Mesa, AZ (US)

(73) Assignee: SpringActive, Inc., Tempe, AZ (US)

(*) Notice: Subject to any disclaimer, the term of this patent is extended or adjusted under 35 U.S.C. 154(b) by 522 days.

(21) Appl. No.: 16/801,341

(22) Filed: Feb. 26, 2020

(65) Prior Publication Data

US 2020/0268542 A1 Aug. 27, 2020

Related U.S. Application Data

(60) Provisional application No. 62/811,447, filed on Feb. 27, 2019.

(51) Int. Cl.
*A61F 5/02* (2006.01)
*A61B 5/11* (2006.01)
(Continued)

(52) U.S. Cl.
CPC ............ *A61F 5/026* (2013.01); *A61B 5/1116* (2013.01); *A61F 5/0102* (2013.01); *A61F 5/024* (2013.01); *B25J 9/0006* (2013.01)

(58) Field of Classification Search
CPC .. A61F 5/00; A61F 5/01; A61F 5/0102; A61F 5/02–028; A61B 5/00;
(Continued)

(56) References Cited

U.S. PATENT DOCUMENTS 807,908 A 12/1905 Bradstreet
1,544,162 A * 6/1925 La Vigne ................. A61F 5/02
2/44
(Continued)

FOREIGN PATENT DOCUMENTS

WO 2014109799 A1 7/2014
WO 2014194257 A1 12/2014

OTHER PUBLICATIONS

"Delta Harness", Harnessland, Mar. 28, 2014. (Year: 2014).
Holgate, M. et al., U.S. Appl. No. 16/655,221, Preloaded Personal Augmentation Suit and Method for Assisted Human Motion.

*Primary Examiner* — Michelle J Lee
(74) *Attorney, Agent, or Firm* — Robert D. Atkins; Patent Law Group: Atkins and Associates, P.C.

(57) ABSTRACT

A human motion assistance device has upper back straps and is configured to attach to a user. A leg strap arrangement with lower back straps is configured to attach to the user. A differential assembly is connected between the upper back straps and lower back straps to reduce resistance of the upper torso harness and leg strap arrangement during gait. When crouching or lifting, the differential assembly transfers force to stretch and retract the upper torso harness and leg strap arrangement, which provides human motion assistance. The differential assembly can be implements as an x-bar, lever arm, pulley, gears, or tube. The leg strap arrangement has a knee pad adapted to cover a knee of the user. The knee pad opens along a segment. The upper torso harness has a shoulder strap and buckle. The leg strap arrangement is an elastic material.

14 Claims, 19 Drawing Sheets

(51) Int. Cl.
*A61F 5/01* (2006.01)
*B25J 9/00* (2006.01)

(58) Field of Classification Search
CPC ......... A61B 5/103; A61B 5/11; A61B 5/1116;
A61B 5/1117; B25J 9/00; B25J 9/0006;
A63B 21/00; A63B 21/40; A63B
21/4001; A63B 21/4005; A63B 21/4007;
A63B 21/4011–4015; A61H 1/00; A61H
1/001; A61H 1/02; A61H 1/0237–0262;
A61H 2001/0211
See application file for complete search history.

(56) References Cited

U.S. PATENT DOCUMENTS

| | | | |
|---|---|---|---|
| 3,295,517 A | | 1/1967 | Stevens |
| 3,411,500 A | * | 11/1968 | Gatts .................... B64G 7/00 600/20 |
| 4,813,080 A | | 3/1989 | Toso |
| 5,652,957 A | | 8/1997 | Williford et al. |
| 5,716,307 A | | 2/1998 | Vadher |
| 5,857,947 A | | 1/1999 | Dicker et al. |
| 5,993,362 A | | 11/1999 | Ghobadi |
| 6,099,445 A | | 8/2000 | Rovinsky et al. |
| 6,129,691 A | | 10/2000 | Ruppert |
| 6,213,922 B1 | | 4/2001 | Afanasenko et al. |
| 6,436,065 B1 | | 8/2002 | Mitchell |
| 6,450,131 B1 | | 9/2002 | Broman |
| 7,553,266 B2 | | 6/2009 | Abdoli-Eramaki |
| 7,744,511 B2 | | 6/2010 | Grigoriev et al. |
| 7,757,305 B2 | | 7/2010 | Toso |
| 7,931,571 B2 | | 4/2011 | Bernardoni |
| 9,144,252 B1 | | 9/2015 | Kostrzewski |
| 9,351,900 B2 | | 5/2016 | Walsh et al. |
| 10,166,426 B2 | | 1/2019 | Adeeko, Jr. |
| 10,843,332 B2 | | 11/2020 | Walsh et al. |
| 2003/0092545 A1 | | 5/2003 | Koscielny et al. |
| 2006/0048998 A1 | | 3/2006 | Wolner et al. |
| 2006/0229175 A1 | * | 10/2006 | Frappier ............ A63B 21/4025 482/124 |
| 2007/0004570 A1 | | 1/2007 | Afanasenko et al. |
| 2007/0135279 A1 | * | 6/2007 | Purdy ................ A63B 21/4025 482/121 |
| 2009/0011909 A1 | * | 1/2009 | Glisan ................ A63B 21/4009 482/129 |
| 2009/0057360 A1 | | 3/2009 | Demsky |
| 2010/0125230 A1 | | 5/2010 | Hurley |
| 2010/0298746 A1 | | 11/2010 | Shimizu et al. |
| 2013/0045842 A1 | | 2/2013 | Wood |
| 2013/0288863 A1 | | 10/2013 | Yamamoto et al. |
| 2013/0319793 A1 | | 12/2013 | Stibilj |
| 2014/0208490 A1 | | 7/2014 | Freixas |
| 2015/0173993 A1 | | 6/2015 | Walsh et al. |
| 2015/0321339 A1 | | 11/2015 | Asbeck et al. |
| 2016/0107309 A1 | | 4/2016 | Walsh et al. |
| 2016/0183606 A1 | | 6/2016 | Shriver |
| 2016/0220438 A1 | | 8/2016 | Walsh et al. |
| 2016/0346156 A1 | | 12/2016 | Walsh et al. |
| 2017/0027735 A1 | | 2/2017 | Walsh et al. |
| 2018/0093374 A1 | | 4/2018 | Holgate et al. |
| 2019/0030708 A1 | | 1/2019 | Holgate et al. |
| 2019/0343670 A1 | | 11/2019 | Ruprecht et al. |
| 2020/0289357 A1 | * | 9/2020 | Sato ..................... A61H 1/0281 |
| 2021/0077839 A1 | | 3/2021 | Arai et al. |
| 2021/0113412 A1 | | 4/2021 | Holgate et al. |

* cited by examiner

PERSONAL AUGMENTATION SUIT AND METHOD FOR ASSISTED HUMAN MOTION WITH BACK DIFFERENTIAL ASSEMBLY

CLAIM TO DOMESTIC PRIORITY

The present application claims the benefit of U.S. Provisional Application No. 62/811,447, filed Feb. 27, 2019, which application is incorporated herein by reference.

FIELD OF THE INVENTION

The present invention relates in general to a human assistance device, and more particularly, to a personal augmentation suit and method for assisted human motion with a differential assembly on the back of the suit.

BACKGROUND OF THE INVENTION

A variety of human assistance devices provide aid for human motion. Some work tasks and activities demand frequent and heavy lifting or long-term strenuous movement, beyond normal unassisted physical exertion, and can lead to exhaustion and potential injury. In particular, excessive strain on muscles and joints can cause injury to the back, legs, and knees with associated reduction in productivity. The human assistance device as worn by the user is designed to overcome or compensate for the added load or strain and make many work tasks easier to perform.

In one embodiment, the human assistance device uses an exoskeleton with rigid components e.g., linkages and joints, attached to the user's body. The exoskeleton joints are positioned to have an axis of rotation collinear with a natural axis of rotation for adjacent joints. The rigid exoskeleton relies on a framework of linkages connected to the body at select locations via pads and straps to provide the ability to augment human movements that need assistance or otherwise enhance the user's performance, stability, balance, and safety. As the user flexes or extends his limbs, these rigid links move in parallel with the limb, adding considerable inertia to the movement. Unfortunately, the rigid exoskeleton also causes considerable restriction to the user's motion that impedes natural and fluid movement.

In another example, U.S. patent publication 2015/0321339 discloses a soft exosuit that generates forces about one or more joints based on anchor elements and connection elements disposed between the anchor elements. The exosuit uses sensors to determine forces on the anchor or connection elements. Actuators are configured to change tension in the soft exosuit in response to the sensors. The exosuit tends to be complex with an overreliance on active components, such as sensors and actuators, to control its operation. The intricate interconnection of anchor elements, connection elements, sensors, and actuators tend to be expensive to manufacture, difficult to configure, slow in response, and overall low reliability.

The soft exosuit can be worn for long periods of time. The user typically performs a variety of functions while wearing the exosuit, including crouching, lifting, and walking. During gait, the movement of the legs tends to stretch the exosuit and impart resistance on the user, even when not in a lifting action. The resistance caused by gait can be uncomfortable for the user, particularly when wearing the exosuit for long periods of time.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, those skilled in the art will appreciate that the description is intended to cover alternatives, modifications, and equivalents as may be included within the spirit and scope of the invention as defined by the appended claims and their equivalents as supported by the following disclosure and drawings.

Figure 1A:
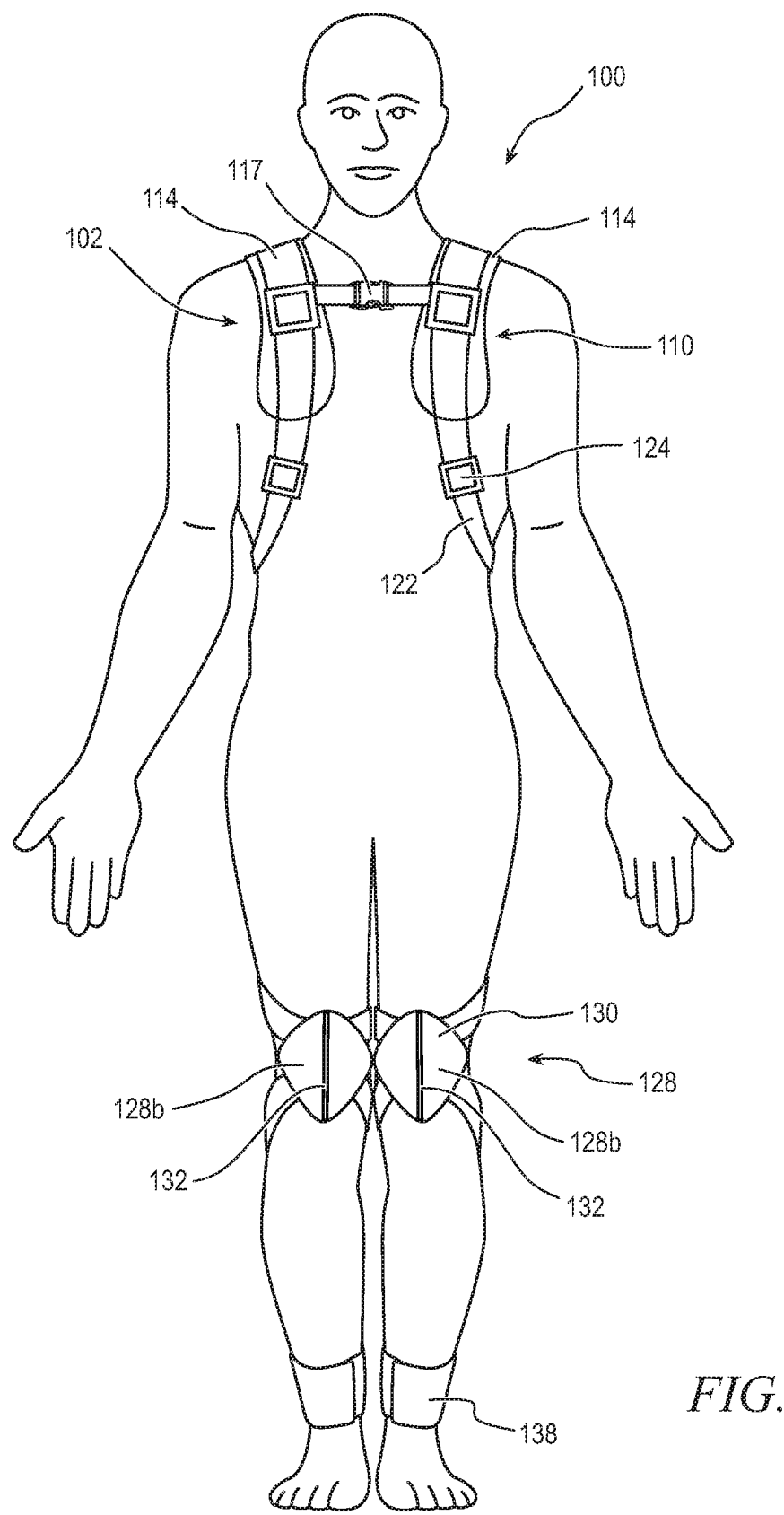
FIGS. 1a-1c illustrate a user wearing a passive P2K suit.
Figure 1B:
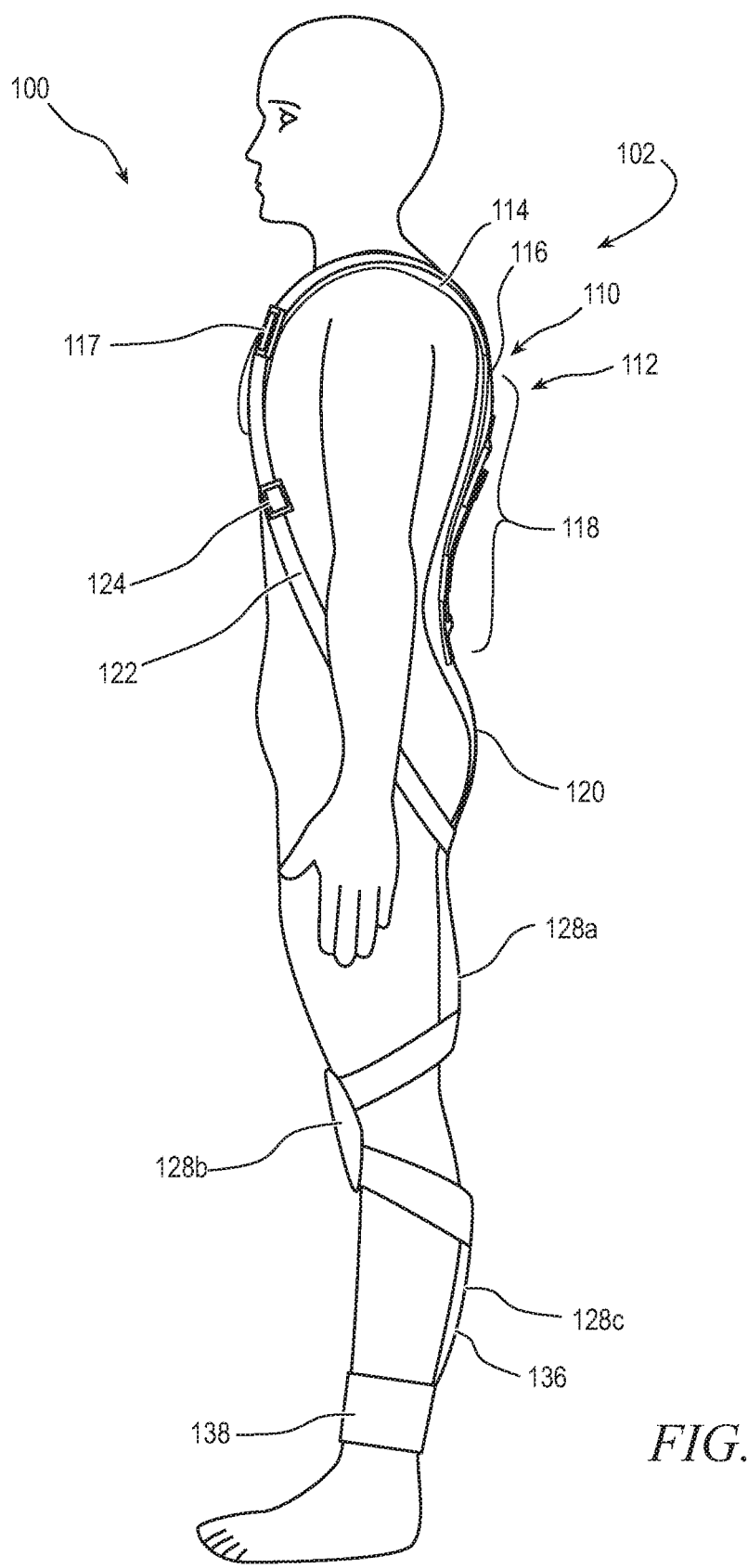
Figure 1C:
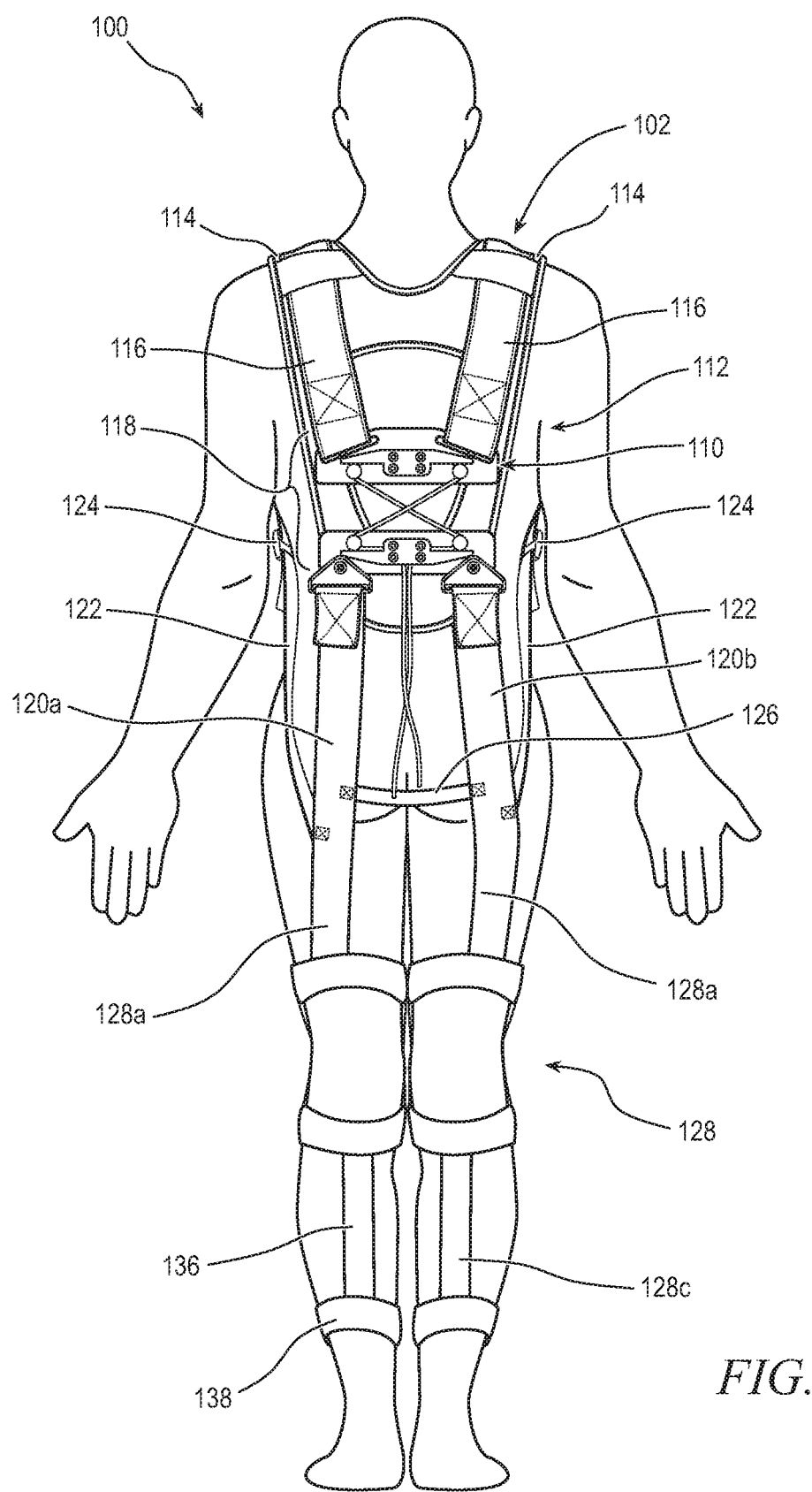

FIG. 1a shows user 100 wearing potential to kinetic suit (P2K) 102 suitable for human assistance in crouching, kneeling, squatting, and lifting under load, as well as normal gait without resistance or discomfort. P2K 102 is a passive personal augmentation suit or strapping system, i.e., no active components, applicable to many types of human activity and physical work, such as moving heavy articles, up and down motion under load, and other repetitive, long-term physical exertion. P2K 102 is capable of storing potential energy in the strapping arrangement, e.g., potential energy is stored in elastic strapping when transitioning from a standing position to a crouched, kneeling, squatting, or seated position. The potential energy in P2K 102 is released when user 100 returns upright in stance, thereby assisting the user in the motion, particularly while under load. P2K 102 increases endurance, reduces fatigue, and decreases potential for injury associated with such activity, particularly for the user's back, legs, and knees. P2K 102 includes an interconnected arrangement of straps, belts, and braces to provide passively loaded support and reaction for user 100, while assisting with human motion under load. P2K 102 further includes a back-mounted differential assembly to enable normal gait for user 100, without resistance or discomfort from the suit. FIG. 1b shows a side view of P2K 102; FIG. 1c shows a back view of P2K 102. Portions of P2K 102 can be reflective material for safety.

Upper torso harness 110 includes backpack assembly 112 with shoulder straps 114 and upper back straps 116. Backpack assembly 112 can include a combination of durable materials such as textured nylon, polyurethane coated polyester, and rigid plastic or polymer inserts, as well as elastic material and webbing material. Backpack assembly 112 can be made with an air mesh material with openings to allow for airflow on the back and reduce the overall weight. Backpack assembly 112 covers a portion of the back area of user 100 to improve ergonomics and comfort, relieve lower back pressure, and ease of donning and doffing. Shoulder straps 114 extend over the shoulder and affix to backpack assembly 112 with sewing, rivets, belt, buckles, buttons, snaps, hooks, adhesive, Velcro®, or other secure attachment mechanism. Shoulder straps 114 are made with elastic material or webbing material and can slide, loosen, or tighten relative to backpack assembly 112 for user comfort and adapting to movement. Buckle 117 in shoulder straps 114 provides adjustment and attachment points. Buckle 117 snaps to lock and enable P2K 102 to fit different body sizes.

Backpack assembly 112 includes differential assembly 118 to enable normal gait activity for user 100, without resistance or discomfort from P2K 102, discussed further infra. Upper back straps 116 continue from shoulder straps 114 to an upper portion of differential assembly 118. Lower back straps 120 extends over the gluteal area and connects to differential assembly 118 with sewing, rivets, belt, buckles, buttons, snaps, hooks, adhesive, Velcro®, or other secure attachment mechanism. Lower back straps 120 slides or moves relative to backpack assembly 112 to enable or minimize medial/lateral relative motion and provide pre-tensioning. Shoulder straps 114 anchor to backpack assembly 112, and side straps 122 extend from backpack assembly 112 under the arms and along the side torso above the hip of user 100 to backpack assembly 112 or lower back straps 120. Side straps 122 can include elastic material with buckles 124 for adjustments and comfort.

Figure 2:
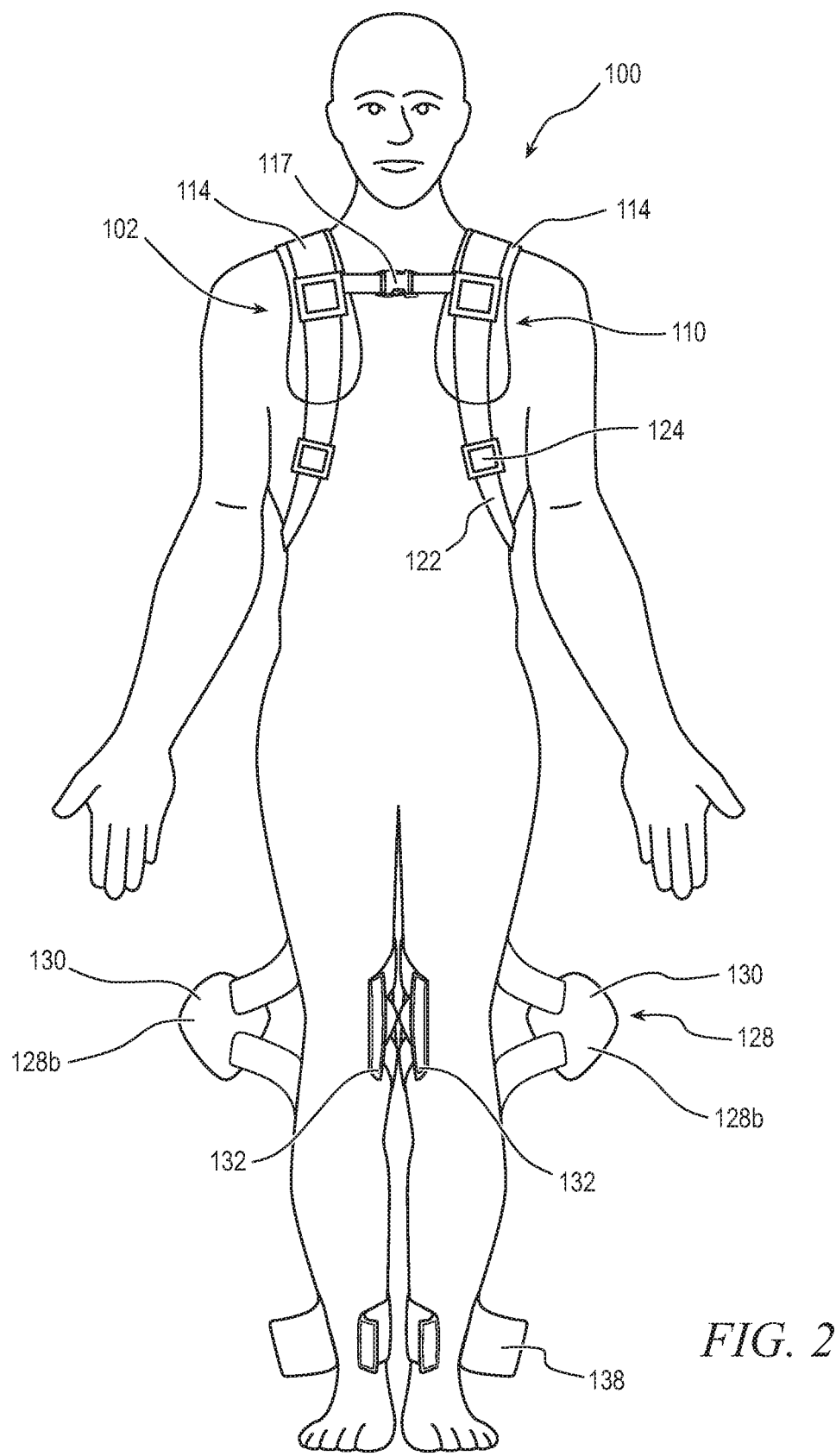
FIG. 2 illustrates the passive P2K suit with the split knee pads and angle straps in the open position.

Leg strap arrangement 128 extends down the legs of user 100. Leg straps 128 include hamstring portion 128a (continuation of lower back straps 120) over the hamstrings of user 100, knee portion 128b over the front of the knee area, and calf portion 128c over the calf area. Hamstring portion 128a connects to lower back straps 120a (left side) and 120b (right side) with sewing, rivets, belt, buckles, buttons, snaps, hooks, adhesive, Velcro®, or other secure attachment mechanism. Seat strap or webbing 126 is connected to lower back straps 120a-120b with sewing, rivets, belt, buckles, buttons, snaps, hooks, adhesive, Velcro®, or other secure attachment mechanism. Seat strap 126 is an elastic or webbing material for storing and releasing power and comfortable load distribution. Knee portion 128b includes knee pads 130 for padding and protection of the knee while kneeling on the ground. Knee portion 128B provides an anchor point during energy storage and return while using P2K 102. In particular, knee pad 130 opens or splits along vertical or angled seam 132 and closes with buttons, snaps, hooks, Velcro®, or other secure attachment mechanism for ease of donning and doffing P2K 102. Leg straps 128 utilize the bending motion of the knee for maximum stretching of the elastic bands. Calf portion 128c includes strap 136 extending down the tibia and strap cuff 138 over the calf. Strap 138 closes with buttons, hooks, snaps, Velcro®, cuff, or other secure attachment mechanism. FIG. 1a shows knee pad 130 and strap cuff 138 in the closed position. FIG. 2 shows knee pad 130 and strap cuff 138 in the open position. The combination of shoulder strap buckle 117, split knee pads 130, and calf strap cuff 138 provide for ease of donning and doffing P2K 102.

The various straps and belts in FIGS. 1a-1c can be implemented using fabric or leather material, elastic bands, cables, or other suitable flexible connecting members. P2K 102 stores potential energy in the strapping arrangement, e.g., the elastic strapping stretches and stores potential energy when transitioning from a standing position to a crouched, squatting, or seated position. The potential energy in P2K 102 remains available while user 100 is seated to help with the opposing motion, i.e., standing up under load. When user 100 stands up from the seated position under load, the potential energy in P2K 102 is released to assist the user in the upward motion. P2K 102 reduces the effort, strain, fatigue, and potential for injury associated with such movement in physical labor work environments.

Figure 3A:
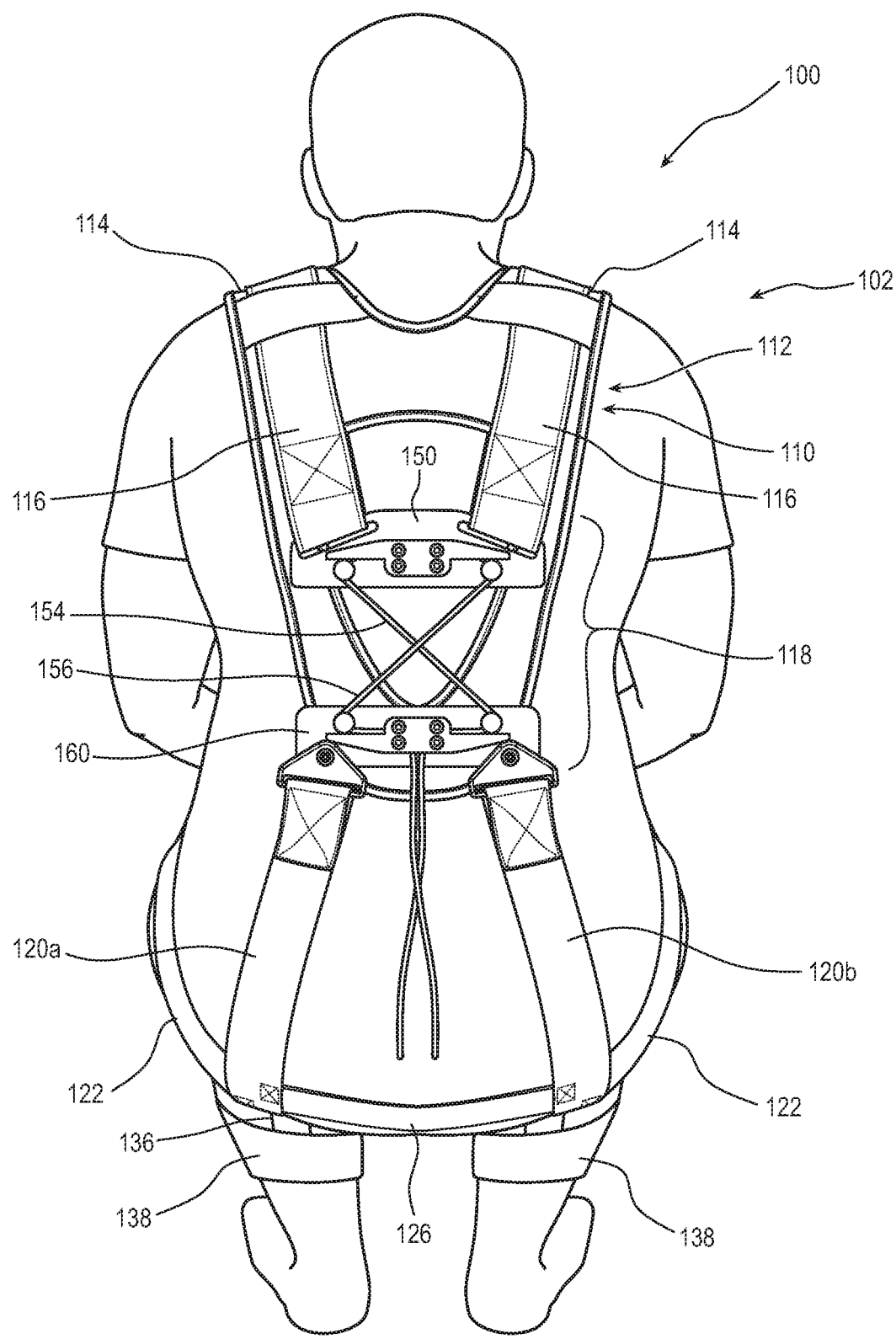
FIGS. 3a-3c illustrate the passive P2K suit activated to assist with lifting a load.
Figure 3B:
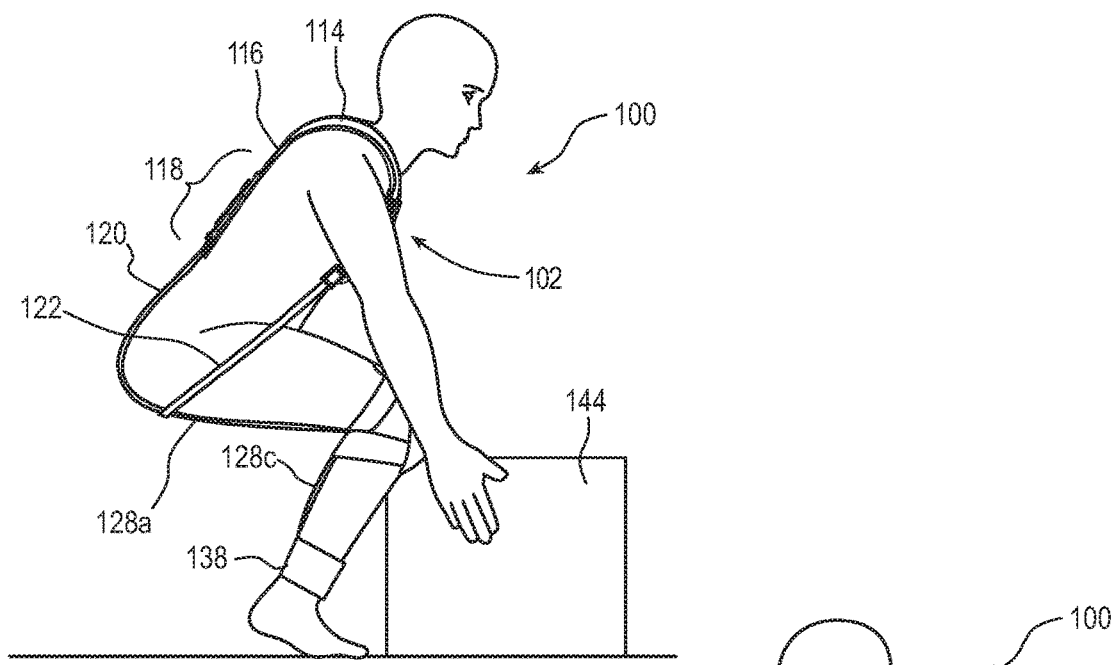
Figure 3C:
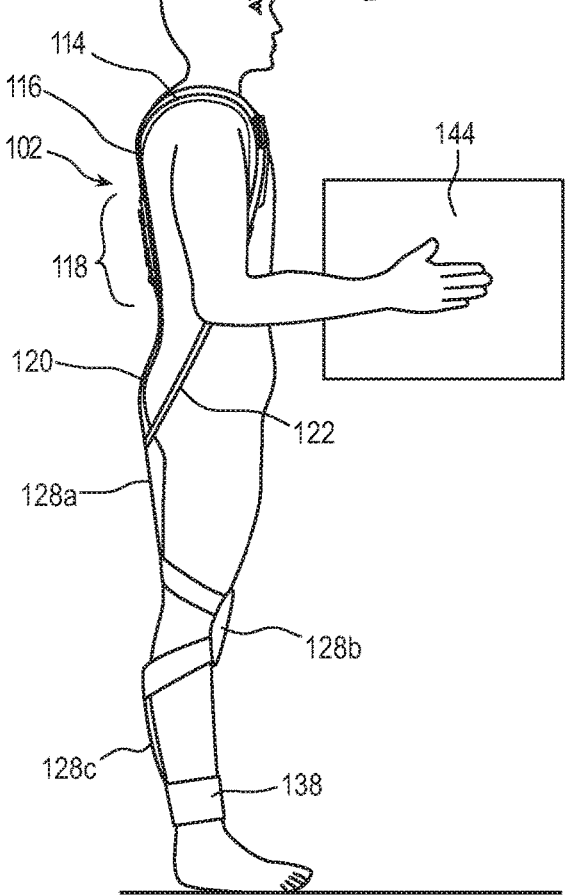

Consider user 100 wearing P2K 102 in a crouching or kneeling position to pick up load 144 in FIGS. 3a-3b. P2K 102 stores potential energy in the strapping arrangement, e.g., the elastic strapping stretches and stores potential energy when transitioning from a standing position to a crouching, kneeling, or seated position. The potential energy in P2K 102 remains available while user 100 is crouching to help with the opposing motion, i.e., standing up under load 144. User 100 stands up from the crouching position with load 144 in FIG. 3c. The potential energy in P2K 102 is released when user 100 moves from the crouching, kneeling, or seated position to return upright in stance, thereby assisting the user in the motion, particularly while under load. P2K 102 reduces the effort, strain, fatigue, and potential for injury associated with such movement in physical labor work environments. In one embodiment, knee pad 130 includes a torsional spring to aid with transition from a seated, kneeling, or crouched position to a standing position, without the use of active components. Alternatively, knee pad 130 uses elastic bands, or a combination of non-elastic and elastic bands, to assist user 100 in the sit to stand transition.

Figure 4:
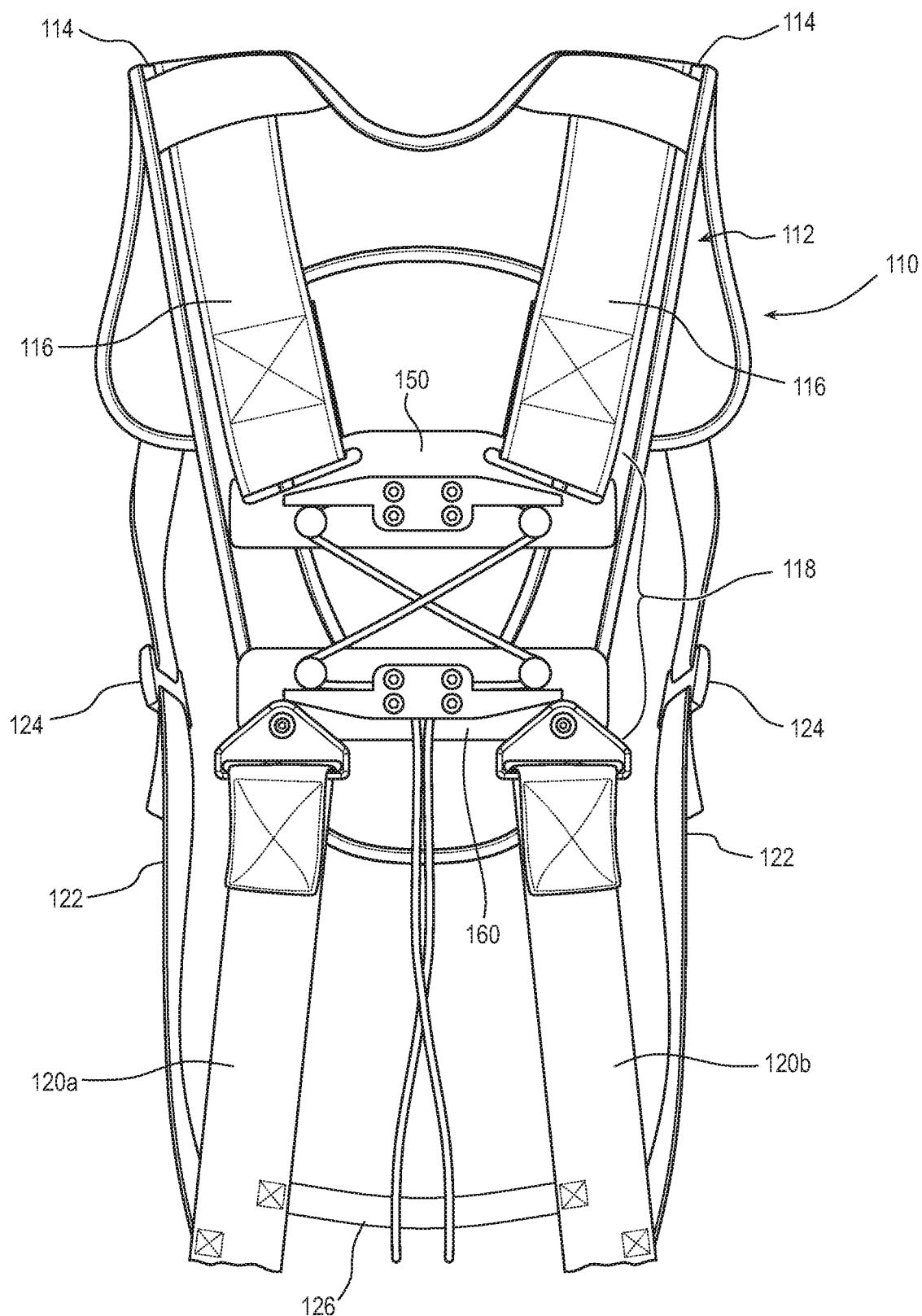
FIG. 4 illustrates further detail of the torso harness with a differential assembly.
Figure 5A:
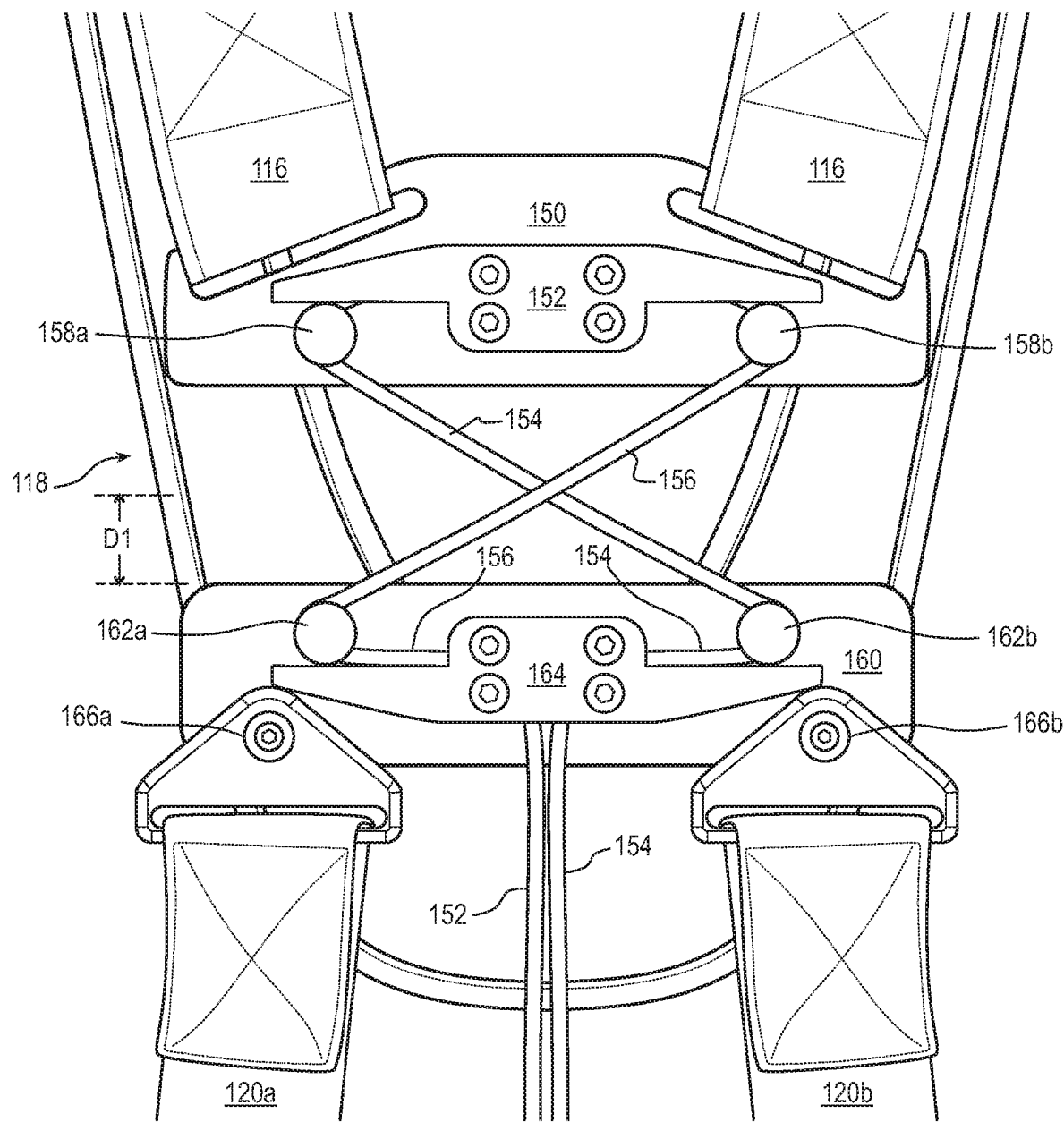
FIGS. 5a-5c illustrate the differential assembly during a lift and gait.

FIG. 4 illustrates another view of a portion of P2K 102 as upper torso harness 110, and in particular with differential assembly 118 connected to upper back straps 116 along horizontal bar 150 and left lower back strap 120a and right lower back strap 120b along horizontal bar 160. In this embodiment, differential assembly 118 is configured as an x-bar to provide support, stretch, and resistance when legs are moved together (crouch and lift), and free motion when legs are moved opposite or independently (gait). When user 100 squats or bends at the waist or knees, the straps of P2K 102 are lengthened. P2K 102 provides assistance by resisting the squatting or bending motions in that straps are on the side of the joint (knee or hip) that lengthens when the joint goes from straight to a bent position. In particular, x-bar type differential assembly 118 includes horizontal bar 150 secured to upper back straps 116 or backpack assembly 112 with anchor 152, as shown in FIG. 5a. Strings or cables 154 and 156 are anchored to bar 150 at points 158a and 158b to make the x-bar. Cables 154 and 156 are routed to horizontal bar 160 and around revolute joints 162a and 162b to anchor 164. Horizontal bar 160 is secured to lower back straps 120a-120b at revolute joints 166a and 166b.

Differential assembly 118 allows the independent or opposite motion of the left and right lower back straps 120a-120b, i.e., during normal gait activity, but does not allow motion through the differential assembly of the left lower back strap 120a and right lower back strap 120b in the same direction, i.e., while squatting or lifting. In other words, differential assembly 118 shifts or tilts in position for opposite motion of the left and right lower back straps 120a-120b (gait), and is held in place by symmetric loading when the right leg and left leg both move up or down together in the same direction with respect to anchor 152 (squat or lift). If the left and right lower back straps 120a-120b move up or down together, e.g., in squatting or lifting motion, then a motion and force is transmitted through differential assembly 118 to stretch P2K 102 for the human motion assistance, as described above and shown in FIG. 5a.

Figure 5B:
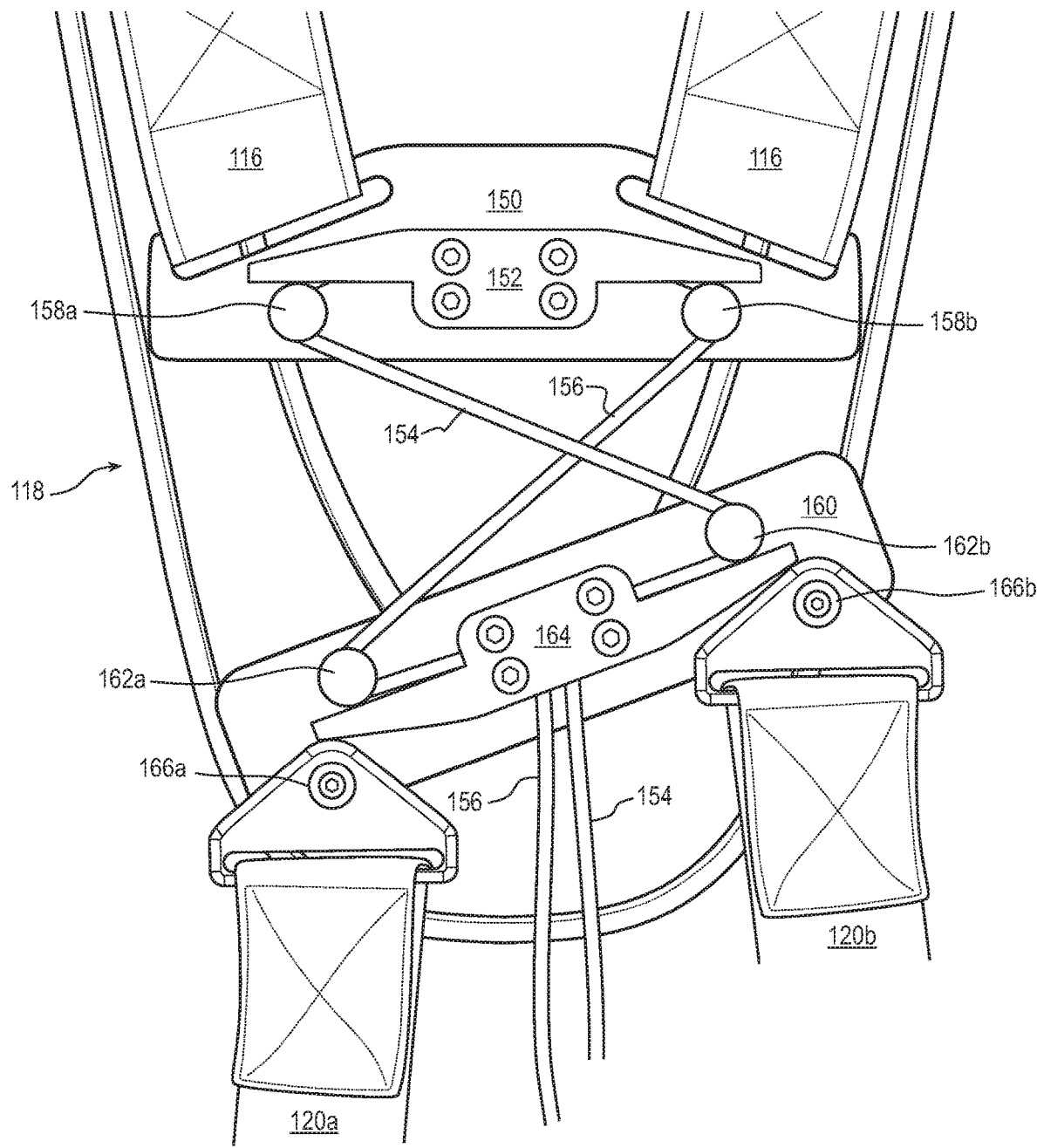
Figure 5C:
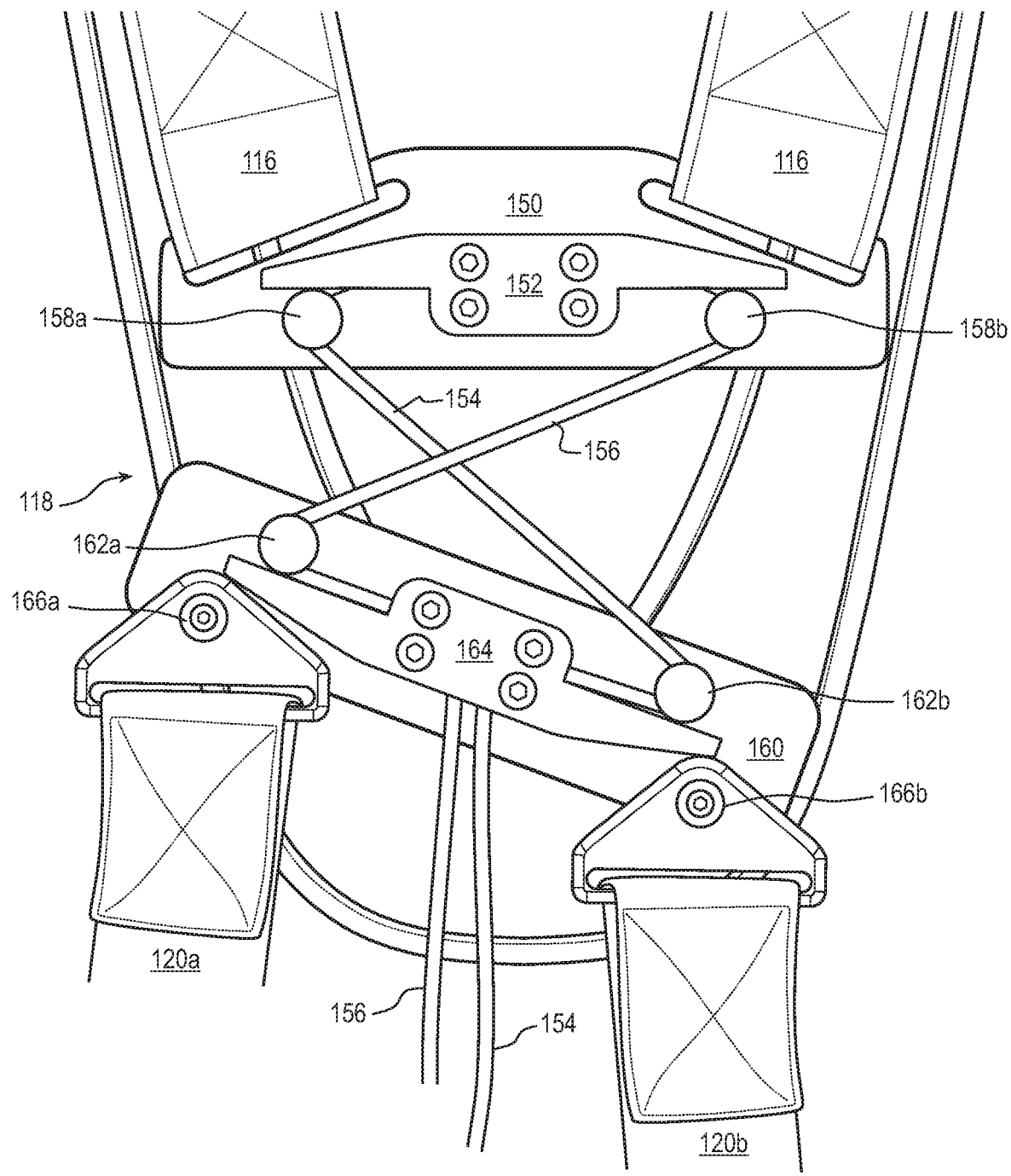

During a first phase of gait, the left leg reaches out and pulls down on the left lower back strap 120a while the right leg lags allowing the right lower back strap 120b to go up, as shown in FIG. 5b. In a second phase of gait, the right leg reaches out and pulls down on the right lower back strap 120b while the left leg lags allowing the left lower back strap 120a to go up, as shown in FIG. 5c. It is preferable to not activate or stretch P2K 102 during gait, which induces unnecessary resistance and would be uncomfortable to user 100. Differential assembly 118 achieves this purpose by allowing the left lower back strap 120a to move down while the right lower back strap 120b moves up, as in FIG. 5b, or the left lower back strap 120a to move up while the right lower back strap 120b moves down, as in FIG. 5c, without activating or stretching P2K 102. When the right or left lower back strap 120a-120b is moved independently or in opposite directions, force is not transmitted through differential assembly 118 to anchor 152. The relative amount of motion between the left and right lower back strap 120a-120b through differential assembly 118 can be the same, i.e., the right moves up by distance D1 and the left moves down by the same distance D1. If differently proportioned, the right moves up by distance D1 and the left moves down by distance D2 different from D1, or one side can move while the other remains stationary. Accordingly, differential assembly 118 reduces resistance from the stretching of P2K 102 while walking, which would be uncomfortable to user 100.

Figure 6A:
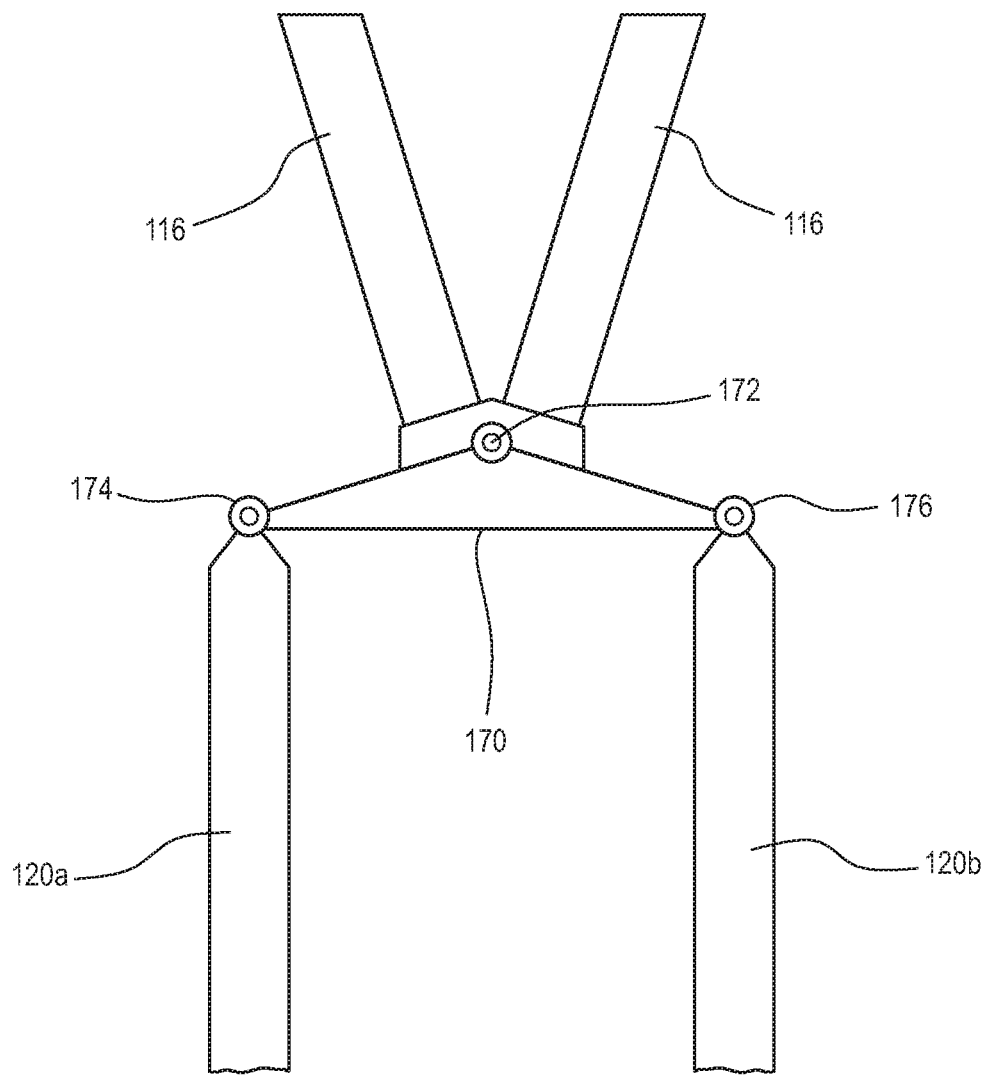
FIGS. 6a-6c illustrate the differential assembly implemented with a lever arm.
Figure 6B:
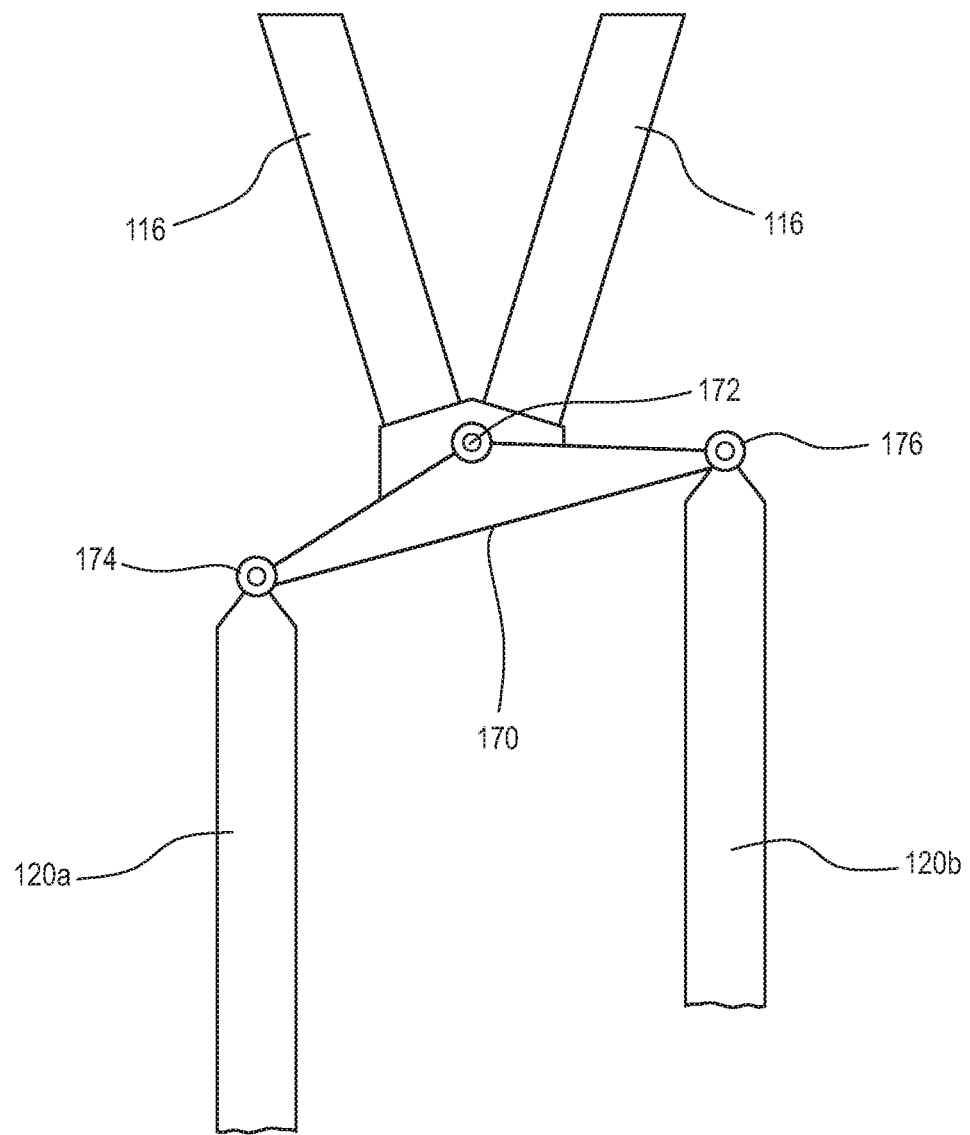
Figure 6C:
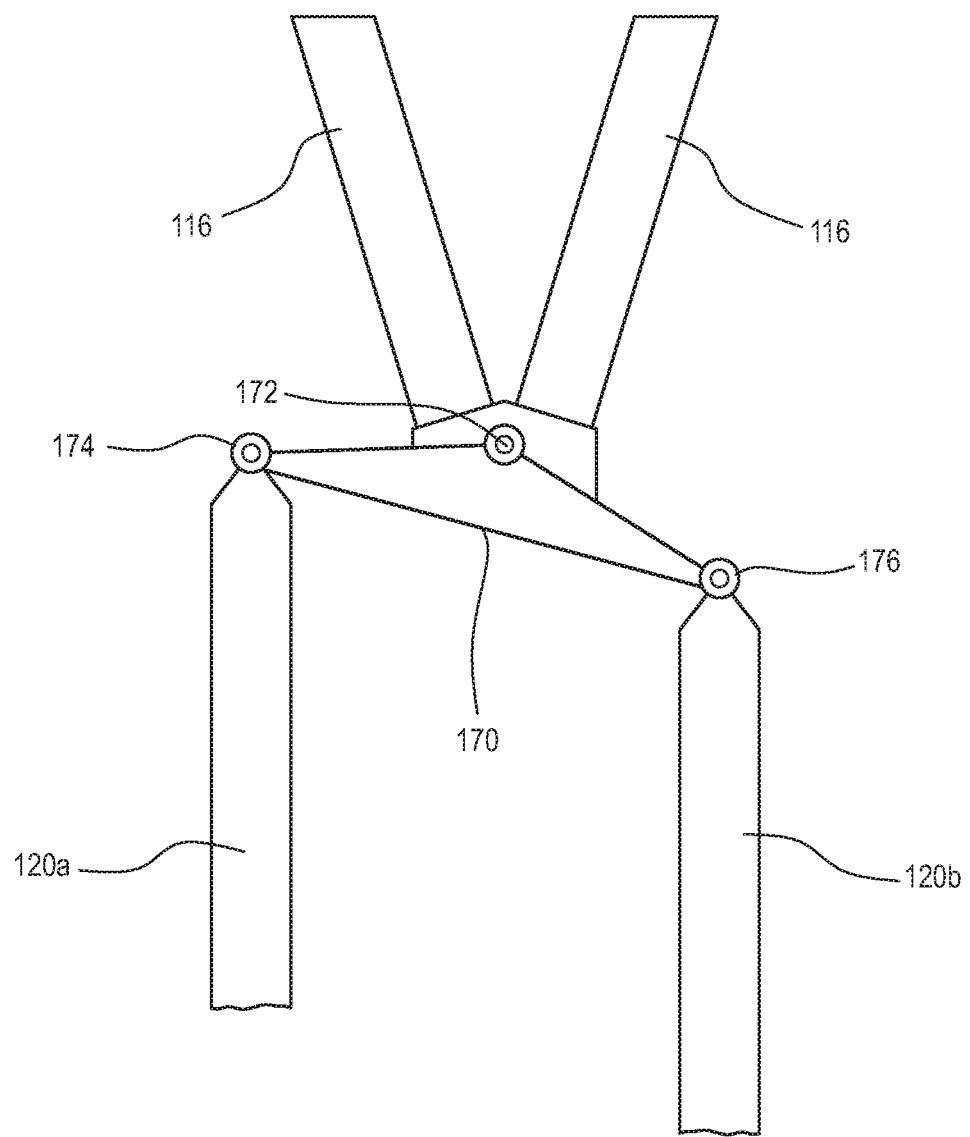

Differential assembly 118 can be implemented using a variety of embodiments. In FIG. 6a, differential assembly 118 is implemented as lever arm 170, which is attached to upper back straps 116 at revolute joint 172, left lower back strap 120a at revolute joint 174, and right lower back strap 120b at revolute joint 176. If the left and right lower back strap 120a-120b move up or down together, e.g., crouch to lift, then lever arm 170 remains level (does not pivot or rotate) and the motion is transferred through the lever arm to stretch P2K 102 for the human motion assistance described above. During gait, when the left lower back strap 120a moves down and the right lower back strap 120b moves up, then lever arm 170 rotates about revolute joints 172, 174, and 176, see FIG. 6b. The left side of lever arm 170 moves down with the left lower back strap 120a, and the right side of lever arm 170 moves up with the right lower back strap 120b. When the left lower back strap 120a moves up and the right lower back strap 120b moves down, then lever arm 170 rotates about revolute joints 172, 174, and 176, see FIG. 6c. The left side of lever arm 170 moves up with the left lower back strap 120a, and the right side of lever arm 170 moves down with the right lower back strap 120b.

Figure 7:
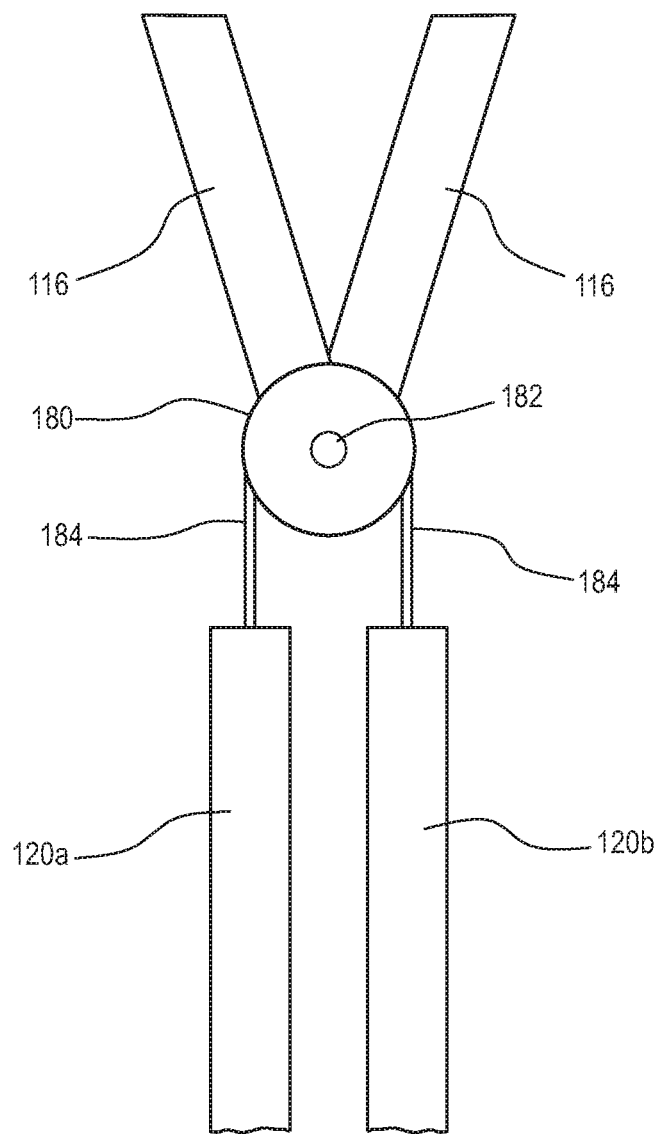
FIG. 7 illustrates the differential assembly implemented with a pulley.

In FIG. 7, differential assembly 118 is implemented as pulley 180, which is attached to upper back straps 116 at revolute joint 182. Cable 184 is routed over pulley 180 and attached to the left lower back strap 120a and right lower back strap 120b. If the left and right lower back strap 120a-120b move up or down together, e.g., crouching to lift, the motion is transferred through pulley 180 (left side of cable 184 does not move relative to the right side of the cable) to stretch P2K 102 for the human motion assistance. During gait, when the left lower back strap 120a moves down and the right lower back strap 120b moves up, then pulley 180 and cable 184 rotate about revolute joint 182. The left side of cable 184 moves down with the left lower back strap 120a, and the right side of cable 184 moves up with the right lower back strap 120b. When the left lower back strap 120a moves up and the right lower back strap 120b moves down, then pulley 180 and cable 184 rotate about revolute joint 182. The left side of cable 184 moves up with the left lower back strap 120a, and the right side of cable 184 moves down with the right lower back strap 120b.

Figure 8:
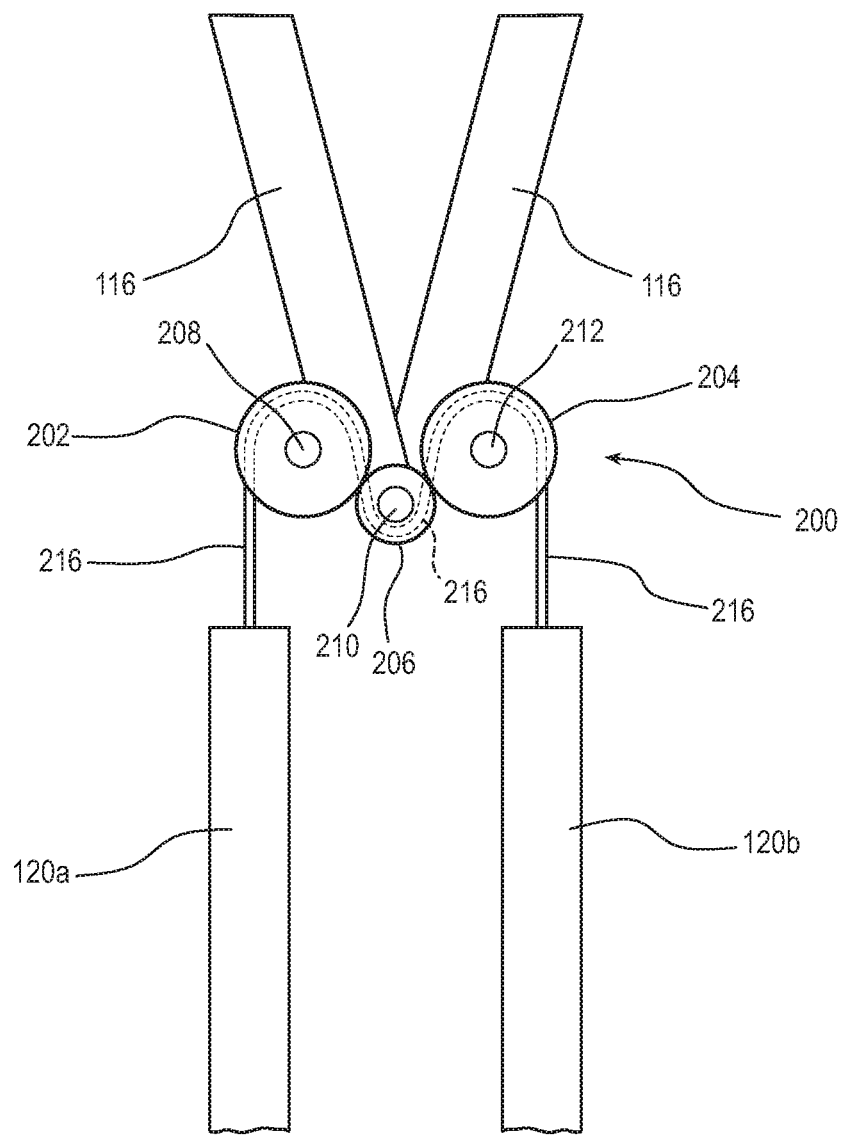
FIG. 8 illustrates the differential assembly implemented with gears.

In FIG. 8, differential assembly 118 is implemented as gear system 200, which uses gears 202, 204, and 206 attached to upper back straps 116 at revolute joints 208, 210, and 212, respectively. Cable 216 is routed over gear 202, under gear 206, and over gear 204, and attached to the left lower back strap 120a and right lower back strap 120b. If the left and right lower back strap 120a-120b move up or down together, e.g., squatting to lift, the motion is transferred through gear system 200 (left side of cable 216 does not move relative to the right side of the cable) to stretch P2K 102 for the human motion assistance. During gait, when the left lower back strap 120a moves down and the right lower back strap 120b moves up, then gears 202-206 and cable 216 rotate about revolute joints 208-212. The left side of cable 216 moves down with the left lower back strap 120a, and the right side of cable 216 moves up with the right lower back strap 120b. When the left lower back strap 120a moves up and the right lower back strap 120b moves down, then gears 202-206 and cable 216 rotate about revolute joints 208-212. The left side of cable 216 moves up with the left lower back strap 120a, and the right side of cable 216 moves down with the right lower back strap 120b.

Figure 9:
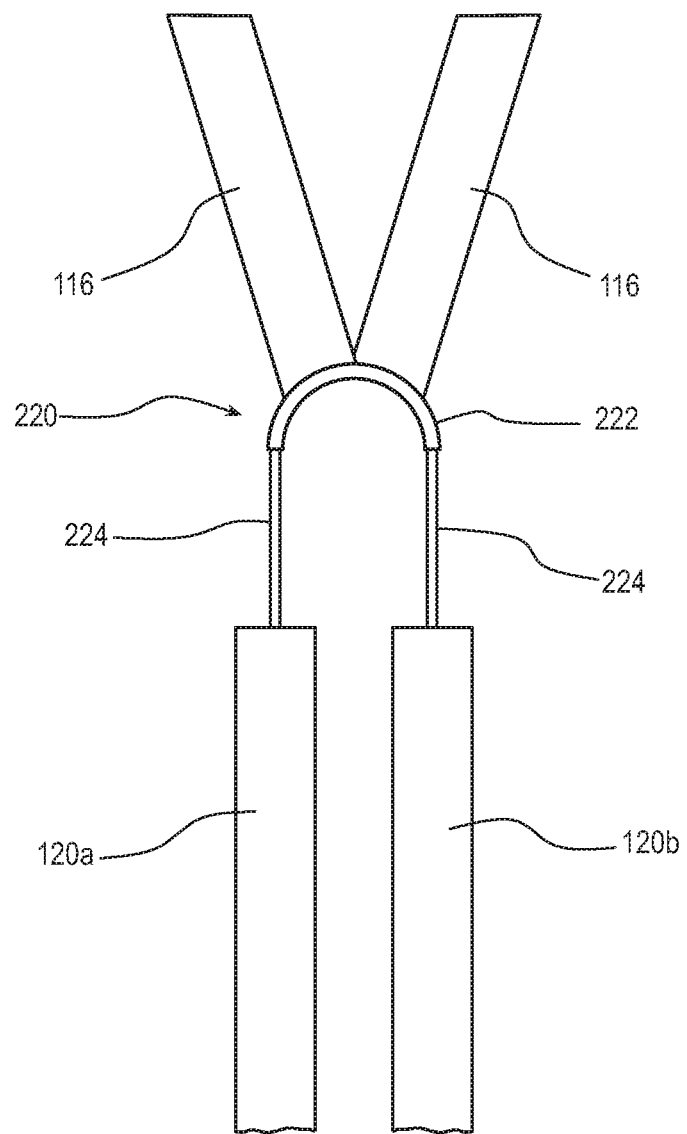
FIG. 9 illustrates the differential assembly implemented with a tube.

In FIG. 9, differential assembly 118 is implemented as channel or tube 220, which is attached to upper back straps 116. Cable 224 is routed through tube 220 and attached to the left lower back strap 120a and right lower back strap 120b. If the left and right lower back strap 120a-120b move up or down together, e.g., squatting to lift, the motion is transferred through tube 220 (left side of cable 224 does not move relative to the right side of the cable) to stretch P2K 102 for the human motion assistance. During gait, when the left lower back strap 120a moves down and the right lower back strap 120b moves up, then cable 224 moves through tube 220 to the left. The left side of cable 184 moves down with the left lower back strap 120a, and the right side of cable 184 moves up with the right lower back strap 120b. When the left lower back strap 120a moves up and the right lower back strap 120b moves down, then cable 224 moves through tube 220 to the right. The left side of cable 184 moves up with the left lower back strap 120a, and the right side of cable 184 moves down with the right lower back strap 120b.

Figure 10A:
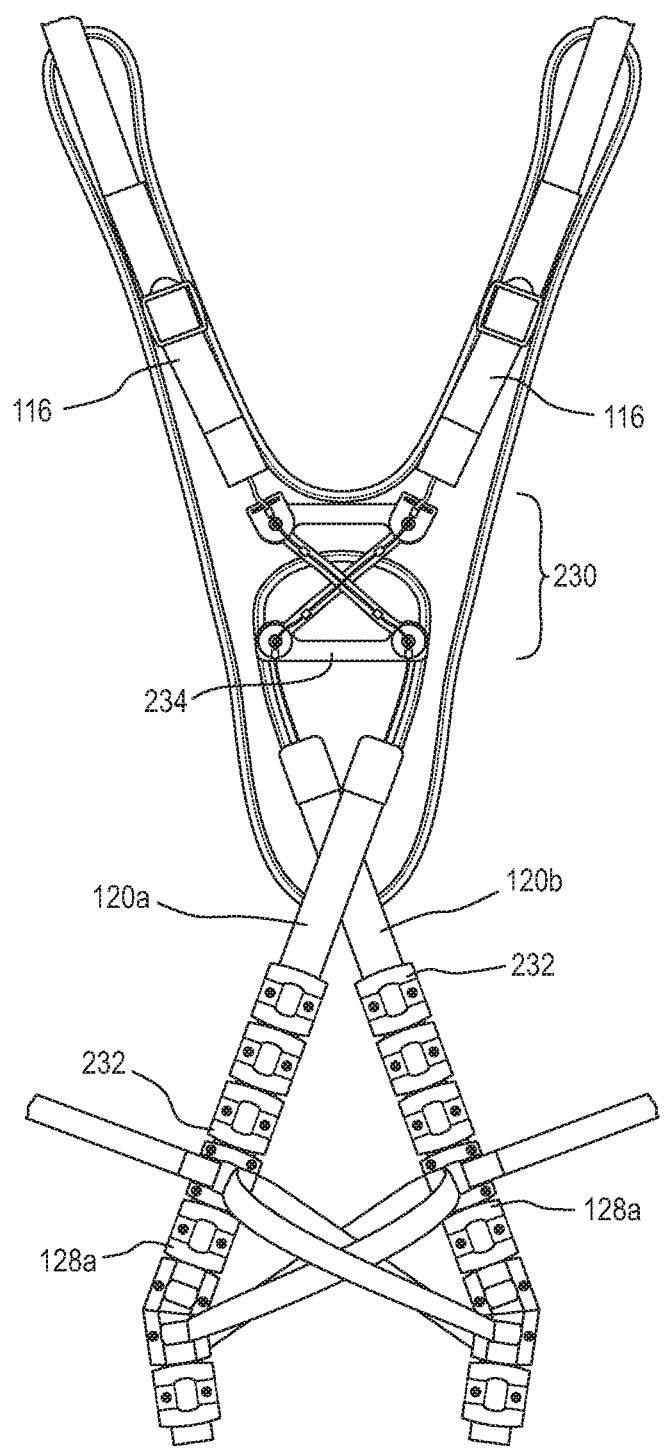
FIGS. 10a-10c illustrate the passive P2K suit with the differential assembly and buckles around the leg straps.
Figure 10B:
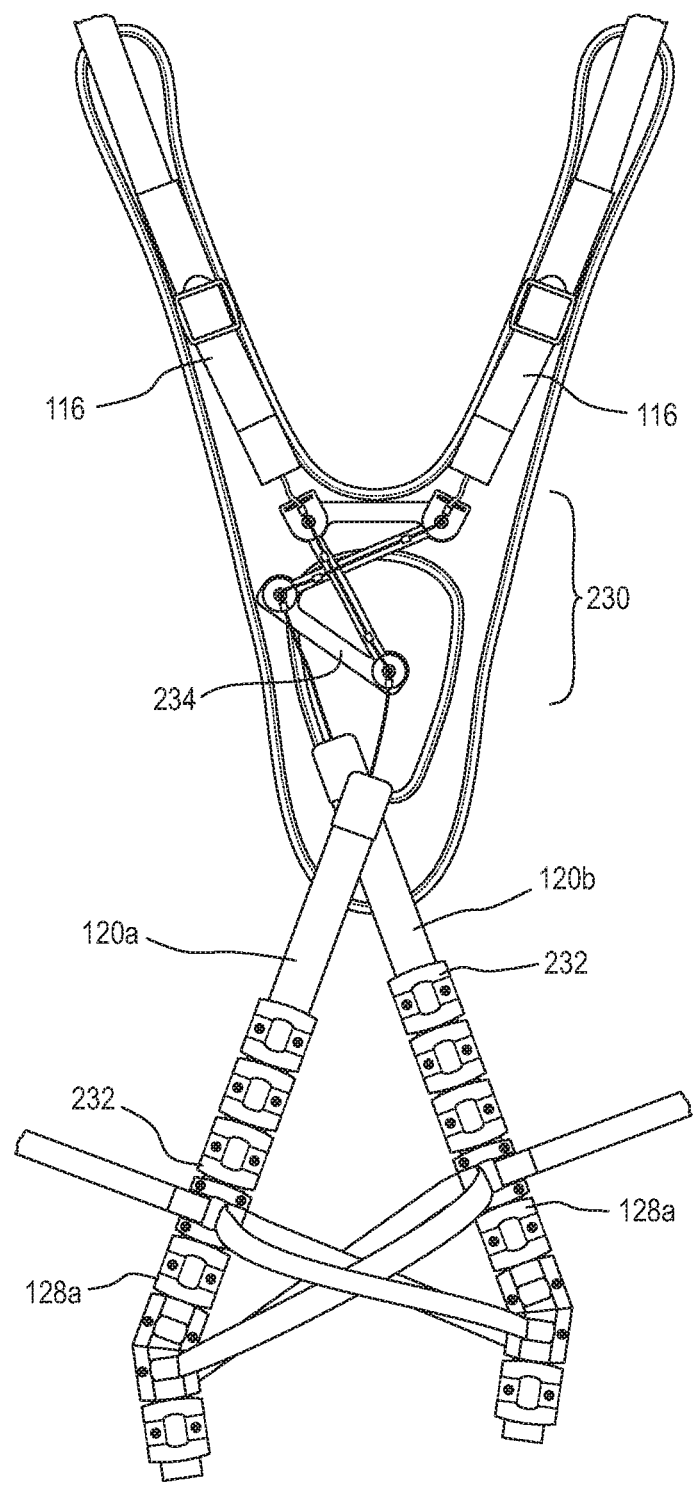
Figure 10C:
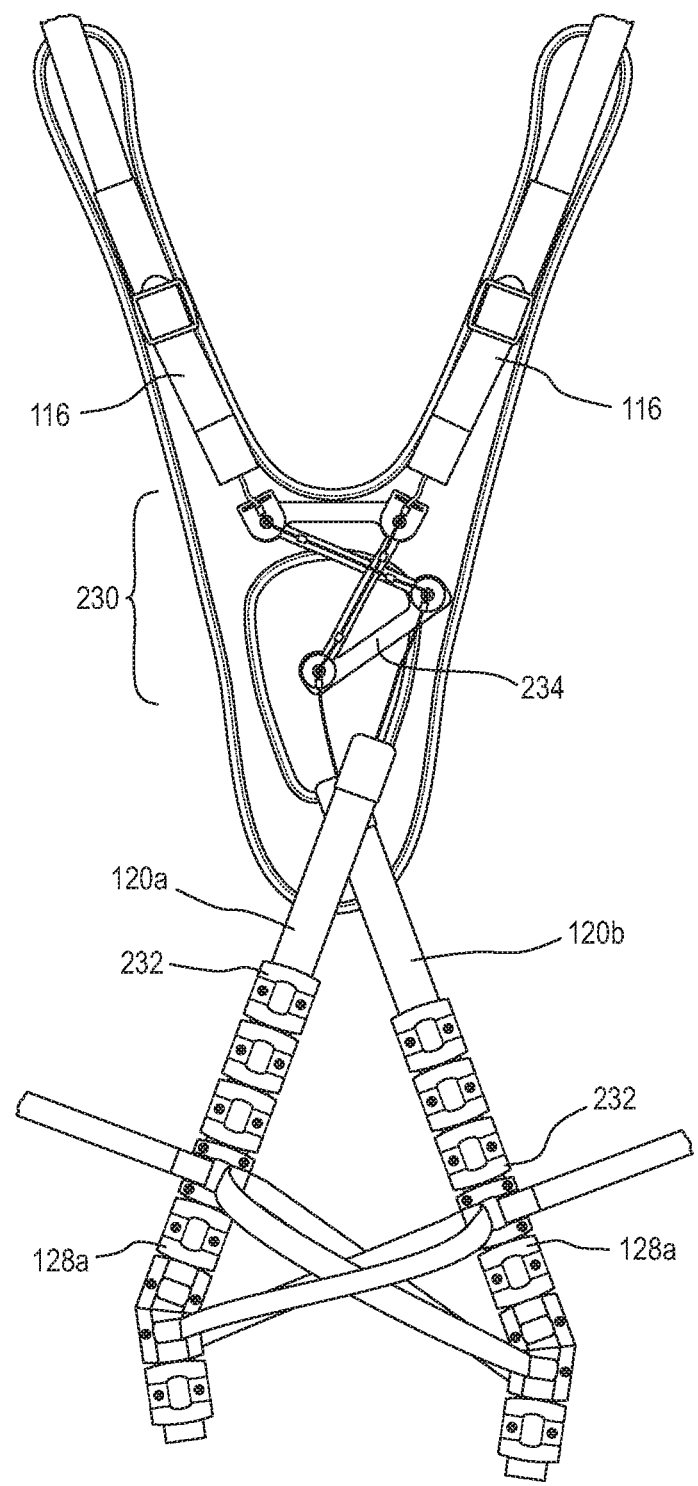

FIG. 10a shown an embodiment with x-bar differential assembly 230 and buckles 232 around leg straps 128. In this case, lower back strap 120a is connected to right side of bar 234 and lower back strap 120b is connected to the left side of bar 234. Buckles 232 are described in U.S. patent application Ser. No. 16/655,221, entitled Preloaded Personal Augmentation Suit and method for Assisted Human Motion, which is incorporated herein by reference. FIGS. 10b-10c shows differential assembly 230 during gait, similar to FIGS. 5b-5c. If the left and right lower back strap 120a-120b move up or down together, e.g., squatting to lift, the motion is transferred through differential assembly 230 to stretch P2K 102 for the human motion assistance. During gait, when the left lower back strap 120a moves down and the right lower back strap 120b moves up, then the right side of bar 234 moves down with the left lower back strap 120a, and the left side of bar 234 moves up with the right lower back strap 120b, see FIG. 10b. When the left lower back strap 120a moves up and the right lower back strap 120b moves down, then the right side of bar 2348 moves up with the left lower back strap 120a, and the left side of bar 234 moves down with the right lower back strap 120b, see FIG. 10c.

While one or more embodiments of the present invention have been illustrated in detail, the skilled artisan will appreciate that modifications and adaptations to those embodiments may be made without departing from the scope of the present invention as set forth in the following claims.

What is claimed:

1. A human assistance device, comprising:
   an upper torso harness with upper back straps configured to attach to a user;
   a leg strap arrangement with left and right lower back straps configured to attach to the user; and
   a differential assembly connected between the upper back straps and left and right lower back straps to reduce resistance of the upper torso harness and leg strap arrangement during gaits;
   wherein the differential assembly includes:
   a first horizontal bar attached to the upper back straps;
   a second horizontal bar attached to the first and second lower back straps;
   a first cable connected between the first horizontal bar and second horizontal bar; and
   a second cable connected between the first horizontal bar and second horizontal bar such that it crosses over the first cable;
   wherein the first and second cables are attached to the second horizontal bar around revolute joints, such that opposite motion of the left and right lower back straps is permitted, but same direction motion of the left and right lower back straps is not permitted.

2. The human assistance device of claim 1, wherein the leg strap arrangement includes a knee pad adapted to cover a knee of the user.

3. The human assistance device of claim 2, wherein the knee pad opens along a segment.

4. The human assistance device of claim 1, wherein the upper torso harness includes a shoulder strap and buckle.

5. The human assistance device of claim 1, wherein the leg strap arrangement includes an elastic material.

6. A method of making a human assistance device, comprising:
   providing an upper torso harness with upper back straps configured to attach to a user;
   providing a leg strap arrangement with first and second lower back straps configured to attach to the user; and
   providing a differential assembly connected between the upper back straps and the first and second lower back straps to reduce resistance of the upper torso harness and leg strap arrangement during gaits;
   wherein providing the differential assembly includes:
   providing a first horizontal bar attached to the upper back straps;
   providing a second horizontal bar attached to the first and second lower back straps;
   providing a first cable connected between the first horizontal bar and second horizontal bar; and
   providing a second cable connected between the first horizontal bar and second horizontal bar such that it crosses over the first cable;
   wherein the first and second cables are attached to the second horizontal bar around revolute joints, such that opposite motion of the left and right lower back straps is permitted, but same direction motion of the left and right lower back straps is not permitted.

7. The method of claim 6, wherein providing the leg strap arrangement includes providing a knee pad adapted to cover a knee of the user.

8. The method of claim 7, wherein the knee pad opens along a segment.

9. The method of claim 6, wherein providing the upper torso harness includes providing a shoulder strap and buckle.

10. The method of claim 6, wherein the leg strap arrangement includes an elastic material.

11. A human assistance device, comprising:
    an upper torso harness configured to attach to a user;
    a differential assembly attached to the upper torso harness; and
    a leg strap arrangement including left and right lower back straps attached to the differential assembly, wherein the upper torso harness and leg strap arrangement are passive;
    wherein the differential assembly includes:
    a first horizontal bar attached to the upper torso harness;
    a second horizontal bar attached to the leg strap arrangement;
    a first cable connected between the first horizontal bar and second horizontal bar; and
    a second cable connected between the first horizontal bar and second horizontal bar such that it crosses over the first cable:
    wherein the first and second cables are attached to the second horizontal bar around revolute joints, such that opposite motion of the left and right lower back straps is permitted, but same direction motion of the left and right lower back straps is not permitted.

12. The human assistance device of claim 11, wherein the upper torso harness includes a shoulder strap and upper back straps connected to the differential assembly.

13. The human assistance device of claim 11, wherein the leg strap arrangement further includes:
    a knee pad adapted to cover a knee of the user.

14. The human assistance device of claim 11, wherein the leg strap arrangement includes an elastic material.

* * * * *

UNITED STATES PATENT AND TRADEMARK OFFICE
CERTIFICATE OF CORRECTION

PATENT NO. : 11,559,420 B2
APPLICATION NO. : 16/801341
DATED : January 24, 2023
INVENTOR(S) : Matthew A. Holgate et al.

It is certified that error appears in the above-identified patent and that said Letters Patent is hereby corrected as shown below:

In the Claims

Column 7, Claim 1, Line 15, replace the word "gaits" with -- gait --.

Column 7, Claim 6, Line 48, replace the word "gaits" with -- gait --.

Signed and Sealed this
Twenty-eighth Day of February, 2023

Katherine Kelly Vidal
Director of the United States Patent and Trademark Office